(12) United States Patent
Sommer, Jr. et al.

(10) Patent No.: US 7,564,943 B2
(45) Date of Patent: Jul. 21, 2009

(54) METHOD AND APPARATUS FOR SORTING MATERIALS ACCORDING TO RELATIVE COMPOSITION

(75) Inventors: Edward J. Sommer, Jr., Nashville, TN (US); Charles E. Roos, Nashville, TN (US); David B. Spencer, Bedford, MA (US); R. Lynn Conley, Antioch, TN (US)

(73) Assignee: Spectramet, LLC, Bedford, MA (US)

( * ) Notice: Subject to any disclaimer, the term of this patent is extended or adjusted under 35 U.S.C. 154(b) by 0 days.

(21) Appl. No.: 11/498,694

(22) Filed: Aug. 3, 2006

(65) Prior Publication Data

US 2007/0030953 A1    Feb. 8, 2007

Related U.S. Application Data

(63) Continuation-in-part of application No. 11/069,243, filed on Mar. 1, 2005, now Pat. No. 7,099,433.

(60) Provisional application No. 60/549,089, filed on Mar. 1, 2004.

(51) Int. Cl.
   *G01N 23/06*   (2006.01)
   *G01N 15/06*   (2006.01)
   *G01N 23/00*   (2006.01)

(52) U.S. Cl. .............. 378/53; 378/58; 250/390.04
(58) Field of Classification Search ............ 378/45–58, 378/62, 83, 88, 98.8, 98.9, 208; 209/589; 250/390.04, 390.09
   See application file for complete search history.

(56) References Cited

U.S. PATENT DOCUMENTS

| 5,738,224 | A  | * | 4/1998 | Sommer et al. | ............ 209/588 |
| 6,272,230 | B1 | * | 8/2001 | Hiraoglu et al. | ............ 382/100 |
| 6,399,951 | B1 | * | 6/2002 | Paulus et al. | ........... 250/370.13 |
| 6,519,315 | B2 | * | 2/2003 | Sommer et al. | ............... 378/45 |
| 2003/0076924 | A1 | * | 4/2003 | Mario et al. | .................. 378/57 |

\* cited by examiner

*Primary Examiner*—Irakli Kiknadze
(74) *Attorney, Agent, or Firm*—Wyatt, Tarrant & Combs, LLP

(57) ABSTRACT

Disclosed herein is a metal sorting device including an X-ray tube, a dual energy detector array, a microprocessor, and an air ejector array. The device senses the presence of samples in the x-ray sensing region and initiates identifying and sorting the samples. After identifying and classifying the category of a sample, at a specific time, the device activates an array of air ejectors located at specific positions in order to place the sample in the proper collection bin.

11 Claims, 5 Drawing Sheets

METHOD AND APPARATUS FOR SORTING MATERIALS ACCORDING TO RELATIVE COMPOSITION

This application is a continuation-in-part application of U.S. patent application Ser. No. 11/069,243, filed Mar. 1, 2005, now U.S. Pat. No. 7,099,433, entitled "Method and Apparatus for Sorting Materials According to Relative Composition," which is hereby incorporated by reference, which claims benefit of U.S. Provisional Patent Application Ser. No. 60/549,089, filed Mar. 1, 2004, entitled "High speed non-ferrous metal sorting using XRF" which is hereby incorporated by reference in its entirety.

STATEMENT REGARDING FEDERALLY SPONSORED RESEARCH OR DEVELOPMENT

This invention was made with federal grant money under National Science Foundation Small Business Innovation Research program under grant number DMI-0239055. The United States Government has certain rights in this invention.

Be it known that we, Edward J. Sommer, Jr., a citizen of the United States and a resident of Nashville, Tenn., Charles E. Roos, a citizen of the United States and a resident of Nashville, Tenn., David B. Spencer, a citizen of the United States and a resident of Bedford, Mass., and R. Lynn Conley, a citizen of the United States and a resident of Antioch, Tenn. have invented a new and useful "Method and Apparatus for Sorting Materials According to Relative Composition."

BACKGROUND OF THE INVENTION

In the scrap metals recycling industry there is a lack of an environmentally clean low cost technology to reliably segregate post-consumer metal scrap into its various metal constituents. Current practice for sorting aluminum metals from other nonmagnetic metals derived from scrap sources such as automobile shredders is to either sort by hand labor or to introduce the mixed metals into a liquid heavy media where the aluminum floats and the heavier nonmagnetic metals sink. Hand labor is far too slow and very expensive. The heavy media process is capital intensive, has high operating costs, and uses a water slurry mixed with chemicals to raise the specific gravity of the liquid to a value above that of aluminum (2.7 gm/cc). The liquid media requires treatment in a wastewater treatment facility. The resulting sludge composed of grease, oil, dirt, and chemicals poses significant disposal issues as do water discharges. Additionally to be cost effective the heavy media process requires a large installation and is normally deployed as a regional facility. This requires the producers of scrap to ship their metals to this regional facility for separation before the metal products can be shipped to market, whereas if sorting could be accomplished locally the scrap producers could ship directly to market. Elimination of the extra shipping requirement would improve the economics of recycling and remove the burden on our environment caused by the shipping of hundreds of thousands of tons of scrap metals annually to regional heavy media plants.

There have been recent efforts to develop dry environmentally friendly techniques to sort low atomic number light weight metals and alloys such as magnesium (atomic number $Z=12$) and aluminum ($Z=13$) and their alloys from higher atomic number heavier metals such as iron ($Z=26$), copper ($z=29$), and zinc ($Z=30$) and their alloys. One method is to acquire and analyze x-ray fluorescence spectra derived from metals by irradiating metals with excitation x-rays, measuring the resulting x-ray fluorescence emitted from the metals, utilizing spectral information developed from the measurements to identify composition of the metals, and to mechanically sort the metals according to their compositions. This method is exemplified by U.S. Pat. Nos. 6,266,390, 6,519,315, and 6,888,917. Low Z material does not lend itself well to x-ray fluorescence analysis since x-ray photons fluoresced from low Z materials are at low yield and are low energy (~1-2 kev). Because they are low energy they are easily absorbed in air before reaching the detection system. This method also, by nature of the detection system, requires a significant time interval to build and analyze spectral information for each piece of material analyzed. Consequently systems that operate according to this method are limited in throughput rate of materials. For high throughput rates it is desired to have a faster acting analyses system in order to process materials faster and at greater volumes.

Another effort is described in Patent Application Publication No. US2004/0066890 wherein is discussed a process of irradiating materials by x-ray radiation, measuring x-ray transmission values through materials at two different energy levels, and using these measurements to determine the thickness and composition of a material. However, that publication does not reveal how such determinations can be accomplished. That dual energy system, as described, discusses utilizing undisclosed image processing techniques and appears similar to standard security x-ray scanners, such as those used at security checkpoints in airports, which utilize x-ray measurements at two different energy levels to measure thickness and material composition and present on a computer monitor screen a complex image for human visual inspection which is graphically encoded by image intensity and false color mapping to represent thickness and material composition (as described by security x-ray scanner vendor Smith's Heimann). Some such x-ray scanners utilize a physically stacked dual energy x-ray detector array to measure x-ray transmission values through materials over two energy ranges, the fundamental features of which are described by GE Medical Systems in their U.S. Pat. Nos. 4,626,688 and RE 37,536. A stacked dual energy detector utilizes a physical geometry of having a lower energy detector sandwiched with a higher energy detector with a filter, typically a metal layer such as copper, interposed between the two detectors. X-rays to be measured first enter the detector stack into the lower energy detector. Lower energy photons are absorbed by the lower energy detector as they are measured. Mid-energy and higher energy photons pass through the lower energy detector. Mid-energy photons are absorbed in the filter layer between the two detectors while higher energy photons pass through the filter layer and are measured by the higher energy detector at the back of the stack. Other x-ray scanners utilize other types of dual energy detector arrangements, such as side-by-side arrays, examples of which are disclosed in U.S. Pat. Nos. 5,841,832 and 5,841,833.

Still another effort utilizes spectral analysis of plasma evaporated off the surface of metal samples induced by momentarily striking the metals with a focused high power laser beam. This method, referred to as Laser Induced Breakdown Spectroscopy or LIBS, reportedly has been practiced in the U.S. by a metals processing company and is detailed in U.S. Pat. No. 6,545,240 B2. The LIBS process for sorting of metals as they are conveyed in volume through a processing line involves a high level of complexity due in part to requirements to rapidly steer a laser beam to small target points from sample to sample for repeated bursts of laser light and to correspondingly steer spectral acquisition optics from sample to sample in coincidence with the laser beam. This method is very complex and costly.

In sorting of many materials, such as nonferrous automobile scrap, it is very advantageous to be able to sort lighter weight materials (such as aluminum and its alloys) from heavier weight materials (such as iron, copper, and zinc and their alloys). To accomplish such a sort it is not necessary to determine both thickness and composition as the method of US2004/0066890 claims to do and it is not necessary to use complex image processing techniques of US2004/0066890 and as practiced using security x-ray scanners. Instead a determination of relative composition, such as relative average atomic number (Z), suffices to make a very valuable sort of the materials. Determination of relative composition, such as in discriminating high Z materials from low Z materials, is simpler for a detection system to accomplish than is determination of thickness and composition which can require high precision detector signals to be able to discern fine differences in measurements from sample to sample, maintenance of comprehensive detection system calibrations, and use of complex pattern matching algorithms such as those used by human visual inspectors in interpreting processed images produced by security x-ray scanners. At this time it has not been technically possible to duplicate by computerized algorithms the complex visual pattern matching skills used by humans in interpreting processed images produced by dual energy x-ray scanner security systems.

SUMMARY OF THE INVENTION

The present invention discloses a metal sorting device and method of use thereof. The metal sorting device, used to distinguish materials of differing atomic weight, includes an X-ray tube, a dual energy detector array positioned to receive x-rays from the X-ray tube, a microprocessor operationally connected to the dual energy detector array, an air ejector controller operationally connected to the microprocessor, and an air ejector array attached to the air ejector controller. The device may include a conveyor belt disposed between the X-ray tube and the dual energy detector array. Certain embodiments of the invention include an air ejector array having at least two air ejectors. Other embodiments of the invention include an air ejector array having as few as one air ejector and others as many as 128 or more air ejectors. Other embodiments of the invention include a collection bin, or at least two collection bins. In certain embodiments, the device includes a dual energy detector array further including dual energy x-ray detectors and a data acquisition system. In another embodiment the dual energy detector array utilizes stacked dual energy detectors.

One embodiment of the invention includes a method of detecting and sorting materials of differing atomic weight, the method includes providing a sample, placing the sample in a sensing region of a dual energy detector array, detecting the sample in the sensing region, reading a high energy sensor value, reading a low energy sensor value, normalizing the high energy sensor value, normalizing the low energy sensor value, computing a ratio of high energy value to low energy value, correlating the ratio with the normalized high energy value, determining whether the correlation is in a high atomic number region or a low atomic number region, transporting the sample to an air ejection array, and energizing at least one air ejector of the air ejection array.

Thickness is typically not a factor in quality of sorted materials for users of many sorted materials such as nonferrous automobile scrap. Consequently it would be advantageous to have an automated sorting system to measure the relative composition of materials processed through the system directly without regard to thickness of the materials and without applying complex pattern matching techniques through image processing. Determination of relative composition independent of material thickness simplifies computerized identification and sorting algorithms by reducing complications arising from processing additional dual energy transmission information with regard to thickness. In this way the algorithms can operate rapidly, accurately, and robustly to identify materials by relative composition and reliably provide signals to rapid sorting mechanisms to effect sorting of the materials according to their measured relative compositions at high throughput rates of materials. It is an objective of the present invention to provide such method and apparatus for thickness independent measurement of material relative composition with accompanying high throughput sorting of the materials according to relative composition.

The present invention incorporates computerized processing of measurements of amounts of transmission of x-ray photons through materials at two separate energy levels (dual energy detection), as illustrated above by way of example, to distinguish materials of relatively high Z from materials of relatively low Z by comparing results of the processing to an experimentally determined preset threshold level which varies as a function of amount of photon energy transmitted through such materials, and responsive to such determinations activates mechanical sorting mechanisms to segregate the relatively high Z materials from the relatively low Z materials, as is further detailed in the following.

DETAILED DESCRIPTION OF THE INVENTION

Figure 1:
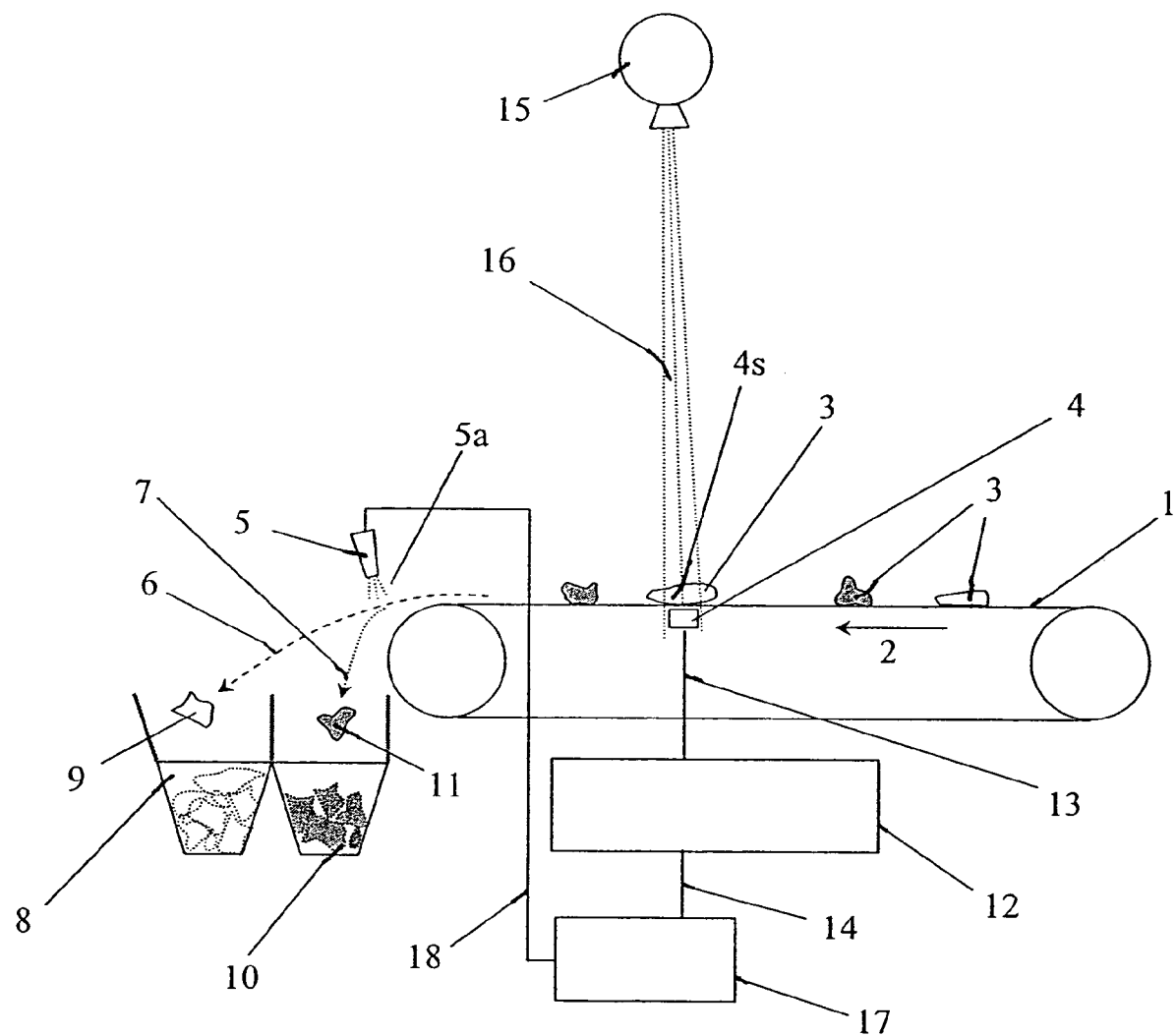
FIG. 1 depicts a side view illustration of a schematic showing mechanical arrangement of portions of an embodiment of the invention.

The present invention uses analyses of x-ray absorptions in a material at differing energy levels in order to determine the relative atomic density (atomic number Z) of the material. X-ray absorption in a material is a function of the atomic density of the material and also a function of the energy of the incident x-rays. A given piece of material will absorb x-rays to differing degrees depending upon the energy of the incident x-rays. Materials of differing atomic numbers will absorb x-rays differently. For instance copper (Z=29) will absorb x-rays much more readily than will aluminum (Z=13). Also the absorption profile of a given piece of copper over a range of x-ray energies will be different than the absorption profile of a given piece of aluminum over that same range of energies. X-ray transmission through a material is given by the equation $$N_{(t)} = N_0 e^{-\eta \rho t}$$

Where $N_{(t)}$ is the number of photons remaining from an initial $N_0$ photons after traveling through thickness t in a material of density ρ. The mass attenuation coefficient η is a property of the given material and has a dependence upon photon energy. The value ηρ is referred to as the mass absorption coefficient (μ) for a given material. Values of the coefficient μ have been established by researchers to high accuracy for most materials and these values are dependent upon the energy of incident x-ray photons. Values of μ/ρ (=η) for most materials can be found at the National Institute of Standards and Technology (NIST) internet website. The lists of values are extensive covering all stable elements for various values of photon energy (kev). The value of ρ for a given material is simply its density in gm/cm³ and can be found in many textbooks and also at the NIST website. The ratio $N_{(t)}/N_0$ is the transmittance of photons through a thickness t of material and is often given as a percentage, ie. the percentage of photons transmitted through the material.

The following table, by way of example, gives values of the mass absorption coefficient μ for aluminum and copper over a range of incident x-ray photon energies and the percentage of photons remaining after passing through 0.2 cm of material (% transmission).

|  | Incident Photon Energy (kev) | Mass Absorption Coefficient μ (cm⁻¹) | % Transmission |
|---|---|---|---|
| Aluminum | 100 | 0.46 | 91% |
|  | 80 | 0.54 | 90% |
|  | 60 | 0.75 | 86% |
|  | 50 | 0.99 | 82% |
|  | 40 | 1.53 | 74% |
|  | 30 | 3.04 | 54% |
| Copper | 100 | 4.11 | 44% |
|  | 80 | 6.84 | 26% |
|  | 60 | 14.27 | 5.8% |
|  | 50 | 23.41 | 0.93% |
|  | 40 | 40.95 | 0.03% |
|  | 30 | 97.84 | <0.00% |

Using the information in the table above we can illustrate how aluminum in this case can be differentiated from copper by comparing ratios of % Transmission ($T_E$) at two different photon energy levels. For instance:

Ratios: $T_{100}/T_{50}$=1.11 for aluminum, $T_{100}/T_{50}$=47.3 for copper

The ratio for copper is much higher than that for aluminum. Further, we find that for differing thicknesses of materials it is possible to distinguish between materials of differing Z value by comparing such ratios while correlating to levels of transmission of photon energy through the materials as is discussed in more detail later. This innovative analytical technique allows effectively differentiating between the materials independent of knowing or determining thickness of the materials as is further discussed in reference to FIG. 4.

Figure 2:
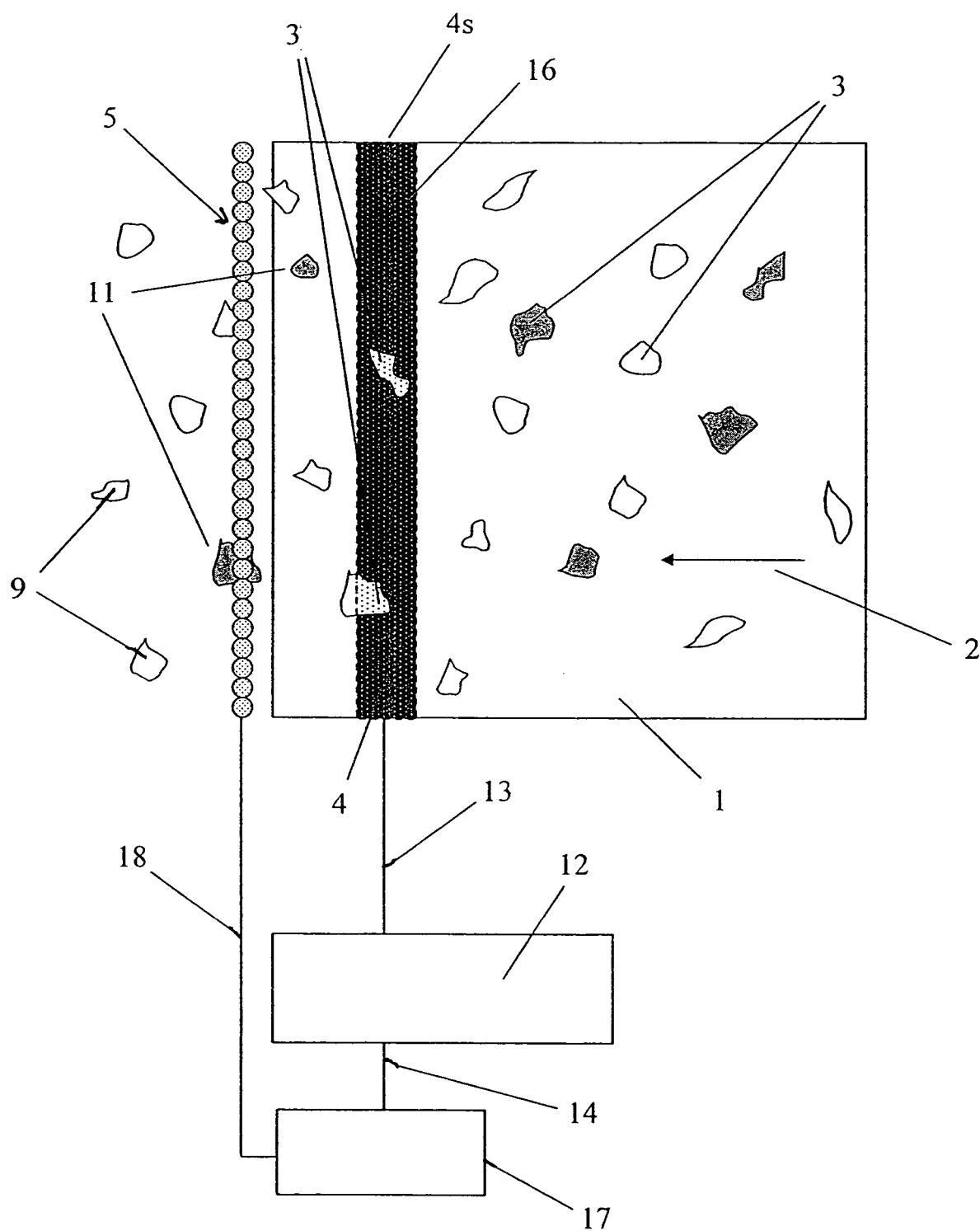
FIG. 2 depicts a top view illustration of the schematic of FIG. 1 showing mechanical arrangement of portions of an embodiment of the invention.

FIG. 1 shows a side view and FIG. 2 a top view of a schematic of mechanical arrangement of portions of a preferred embodiment of a materials sorting system of the present invention that incorporates a dual energy x-ray detector array 4 positioned below the surface of a conveyor belt 1 used for transporting materials samples 3 into and through a sensing region 4s located on conveyor belt 1 between detector array 4 and x-ray tube 15. Belt 1 moves in a direction as shown by arrow 2 in FIG. 1 and FIG. 2. Detector arrays suitable for this use can be obtained from Elekon Industries, Torrance, Calif. X-ray tubes may be obtained from Lohmann X-ray, Leverkusan, Germany. Materials samples 3 may be a mixture of relatively high Z materials 11 (such as metals copper, iron, and zinc and their alloys—depicted by shaded samples) and relatively low Z materials 9 (such as metals magnesium and aluminum and their alloys—depicted by not shaded samples). The x-ray tube 15 is a broadband source that radiates a sheet of preferably collimated x-rays 16 across the width of conveyor belt 1 along the dual energy x-ray detector array 4 such that x-rays pass through sensing region 4s and conveyor belt 1 prior to striking detectors 4. Such a dual energy x-ray detector array 4 is well-known in the art, an example of which is described in detail in GE Medical Systems U.S. Pat. Nos. 6,266,390 and 6,519,315. As materials samples 3 pass through the sheet of x-rays in sensing region 4s x-rays transmitted through them are detected by the dual energy x-ray detector array 4 at two different energy levels. The detection signals are transmitted to computer system 12 over electrical connections 13 and the signals analyzed by a software algorithm 40 (FIG. 5) executing within computer system 12 to determine relative composition of samples 3 with respect to a preset relative composition level 35 (FIG. 4), as will be discussed in more detail later. In the example shown computerized algorithm 40 processes measurements of transmission levels of x-rays through materials at two energy levels using data from detector array 4 and makes a classification of each material sample 3 as being a relatively low Z material 9 or as being a relatively high Z material 11 with respect to preset relative composition level 35 and selects either low Z materials 9 or high Z materials 11 for ejection from the stream. Downstream from the sensing region 4s, located just off the discharge end of the conveyor belt 1 and positioned across the width of the trajectory paths 6,7 of materials discharged off the end of conveyor belt 1, is an array of high speed air ejectors 5, such as the L2 series supplied by Numatics, Highland, Mich., which are controlled by computer system 12, responsive to the algorithm 40 computations, by signaling air ejectors controller 17 through connections 14 to selectively energize through connections 18 appropriate air ejectors within air ejectors array 5 to deflect by short air blasts 5a selected materials from the flow. In the example shown relatively high Z metals 11 are selected for ejection along trajectories 7 into the metal group1 bin 10 and relatively low Z metals 9 pass unejected along trajectories 6 into metal group2 bin 8. It is noted that the system can just as easily be configured by the user through a standard control interface (not shown) to eject low Z materials into group1 bin 10 and let high Z materials pass unejected into group2 bin 8. It will be apparent to those skilled in the art that three or more bins could be utilized using multi-directional air ejectors or other sorting means. The sequence of sensing, selection, and ejection can happen simultaneously in multiple paths along the width of the conveyor belt 1 so that multiple metal samples 3 can be analyzed and sorted coincidentally as indicated in FIG. 2.

Figure 3:
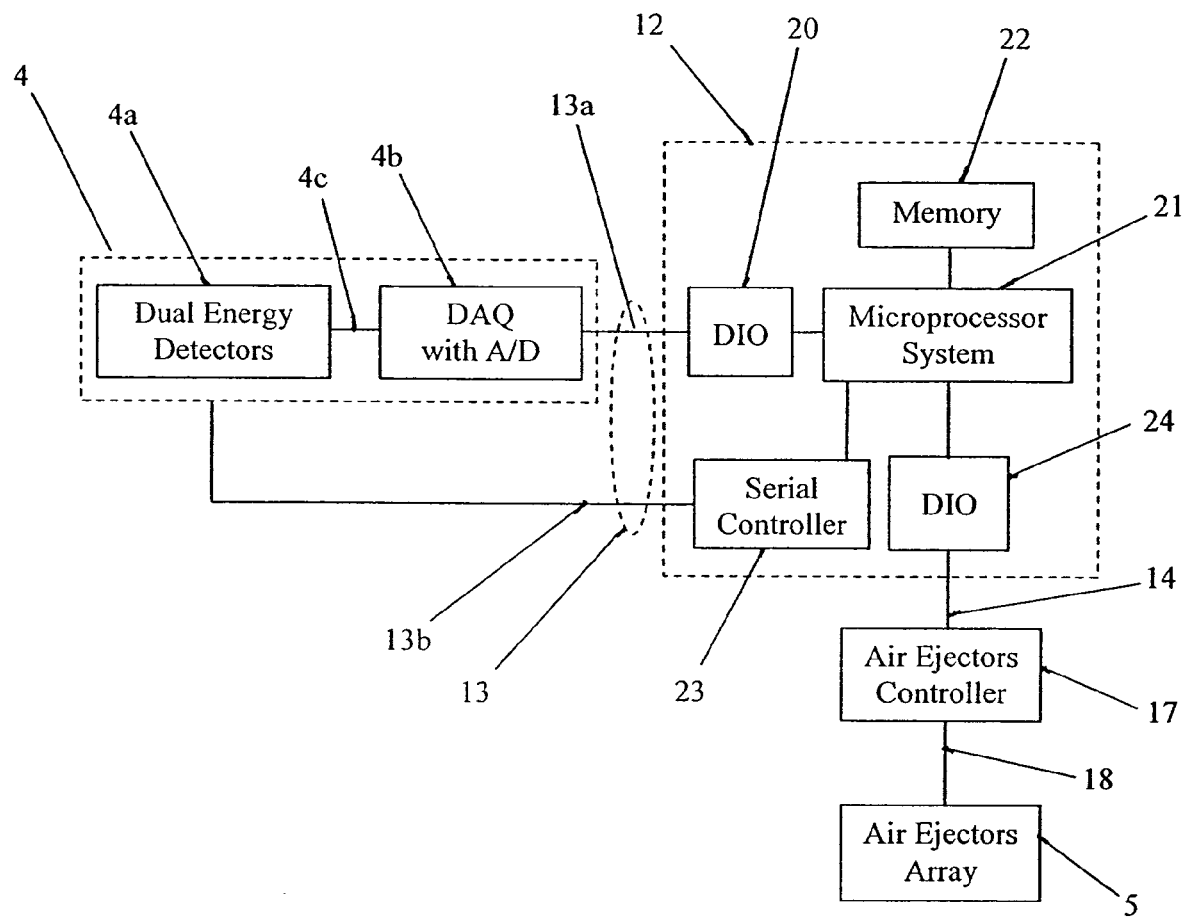
FIG. 3 shows a block diagram for an embodiment of the invention illustrating relationships between various portions of the electrical/computer hardware for acquiring and processing x-ray detector signals and for activating selected air valves within an air ejector array responsive to the results of the processing.

FIG. 3 shows a block diagram for an embodiment of the invention illustrating relationships between various portions of the electrical/computer system for acquiring and processing x-ray detector signals and for activating selected air valves within air ejector array 5 responsive to the results of the processing. The dual energy detector array 4 in this embodiment includes within its circuitry the dual energy x-ray detectors 4a and a data acquisition system (DAQ) with analog to digital (A/D) circuitry 4b for acquiring analog signals from the detectors over connections 4c and converting these signals to digital signals. The digital signals are transmitted over connections 13a, which are part of the electrical connections 13 between computer system 12 and dual energy array 4, to digital input/output (DIO) module 20. For this data transfer the input function of module 20 is utilized. Internal to computer system 12 DIO module 20 passes the digital data to microprocessor system 21. Microprocessor system 21 may be a single microprocessor or a system of multiple microprocessors linked together to share computational tasks to enable high speed data processing as is the case for this preferred embodiment. A suitable multiple microprocessor system is the Barcelona-HS available from Spectrum Signal Processing, Burnaby, Canada. Microprocessor 21 provides control signals to dual energy array 4 through serial controller 23 over electrical connection 13b. Materials classification and sorting algorithm 40 (FIG. 5), which is discussed in more detail later, executes within microprocessor system 21 processing digital data received from dual energy array 4 and utilizes computer memory 22 for storing data and accessing data during execution. According to results derived through executing of algorithm 40 microprocessor system 21 signals air ejectors controller 17, for example a bank of solid state relays such as those supplied by Opto22, Temecula, Calif., through DIO module 24 to energize selected air ejectors within air ejector array 5 over connections 18 so to eject from the flow of materials 3 selected materials 11 according to computed relative composition as the materials are discharged off the discharge end of conveyor 1. The user of the sorting system may chose through a standard control interface (not shown) for ejected materials 11 to be relatively high Z materials or relatively low Z materials, compared to preset relative composition level 35 (stored in memory 22) as determined by algorithm 40.

The x-ray technology of the present invention measures changes in amount of x-ray transmission through an object as a function of energy. This technology can evaluate the entire object and looks through the entire object taking into consideration exterior and interior variations. The technology evaluates how the quantities of transmitted x-rays at various energy levels change as a function of the incident x-ray energy. One embodiment may be a multi-energy cadmium zinc telluride (CZT) pixel detection system arranged into a linear detector array of very small size is suitable to collect x-ray transmission information at each detector site and transmit it to an on-board computer system to collect data from multiple sensors simultaneously. Another embodiment may be an arrangement of multiple individual multi-energy detection systems such as those provided by Amptek, Bedford, Mass. Such systems could provide a greater number of energy bins. Multiple sub-systems could cover a wide conveyor belt. The data from the multi-detector array will provide multi-energy readings from each detector to provide an energy dispersive x-ray transmission profile of an object for assessing composition of a broad range of matter. Such a multi-energy CZT linear detector array having 32 CZT detectors at 0.5 mm pitch is available with supporting electronics from Nova R&D, Riverside, Calif. Each detector in the Nova R&D detection system can read and report x-ray transmission levels at up to five energy bands simultaneously at high rates of data acquisition and this capability is expected to expand to more energy bands as the technology is further developed. Further, the detectors have a spatial resolution of 0.02 inches per pixel in the array allowing detailed high resolution multi-energy profiling of x-ray transmission through an object under inspection. In effect one can build a high resolution multi-energy image of an object under inspection as the object is conveyed through the inspection region as well as simultaneously measuring the relative average atomic number of bits of matter within the image.

Such a system is functionally analogous to a line-scan camera commonly found in industrial inspection processes. Whereas a line-scan camera detects multiple "colors" within the visible spectrum, the system of the present invention detects "colors" within the x-ray spectrum. Thus, the system may be characterized as a multi-spectral, x-ray camera providing a much richer data set than the dual energy techniques described in more detail herein. This multi-energy data set allows expanded imaging and material identification capabilities as described in general terms below.

While the new system provides data that can be represented by an x-ray image, an intelligent interpretation of that image is essential to identification and sortation of material. The presence of any atomic element is manifest by spectral peaks (from fluorescence) or discontinuities (from transmission) that result from electron-state transitions unique to that element. Since these peaks or edges occur in spectrally narrow regions (on the order of eV), detection of an element only requires monitoring a small portion of the spectrum. Unfortunately, the absorption edges of "interesting" elements span a wide energy range, from less than 1 keV to more than 80 keV. Additionally, material morphology and composition, processing rates and environment, and sensor response renders peak or edge detection as the exclusive method of sorting a wide variety of materials impractical. Peaks or edges may be used to discriminate among a subset of elements, but it is thought that interrogating a material's spectrum over a shorter energy range (shorter than 1 keV→80 keV) will divulge information sufficient for recycling purposes although a range double that (up to 160 keV) could be useful. In particular, applying derivatives, tangential intersections and spectral correlation to the absorption curve of a material could provide adequate discrimination among categories of recyclables.

When compared to the simple discriminators of difference or ratio, the proposed operations are, in general, more susceptible to noise within the response curve of a material. Thus, to generate meaningful descriptors, mitigating all forms of "noise" is advantageous. Since in one embodiment the system of the present invention measures individual photons, the inherent noise from this method of detection is described by a Poisson distribution and can be reduced by collecting more photons. The nature of the CZT detectors in the Nova R&D linear array system limits the photon counting rate to approximately 50 million counts per second (MCount/Sec): the ensuing electrons further limit this rate to approximately 1 MCount/Sec. New systems under development could extend the counting rate by an order of magnitude (up to 500 MCount/sec). Since sufficiently "smooth" curves may require thousands of counts per acquisition, noise reduction through increased photon counts can result in decreased processing rates.

A material's absorption curve could prove sufficient for identification and sortation. However, certainty during the identification process may be augmented by fluorescence information. When x-rays pass through a material, some x-rays with energies greater than the electron excitation energy of constituent elements are absorbed and re-emitted as fluoresced photons. This process of absorption and re-emission is characterized in the transmission spectrum as an "absorption edge" and a "fluorescence peak," where the peak is always near, but at a slightly lower energy than the edge. In a traditional absorption curve, the fluorescent peak is negligible. However, as a detector is gradually removed from the primary path of x-ray transmission, the signal contribution from primary x-rays are reduced and the contribution from secondary x-rays, such as fluorescence and scatter, are increased. Understandably, fluorescence is considered a "surface" phenomenon, but perhaps this information could enhance identification under certain conditions.

Figure 4:
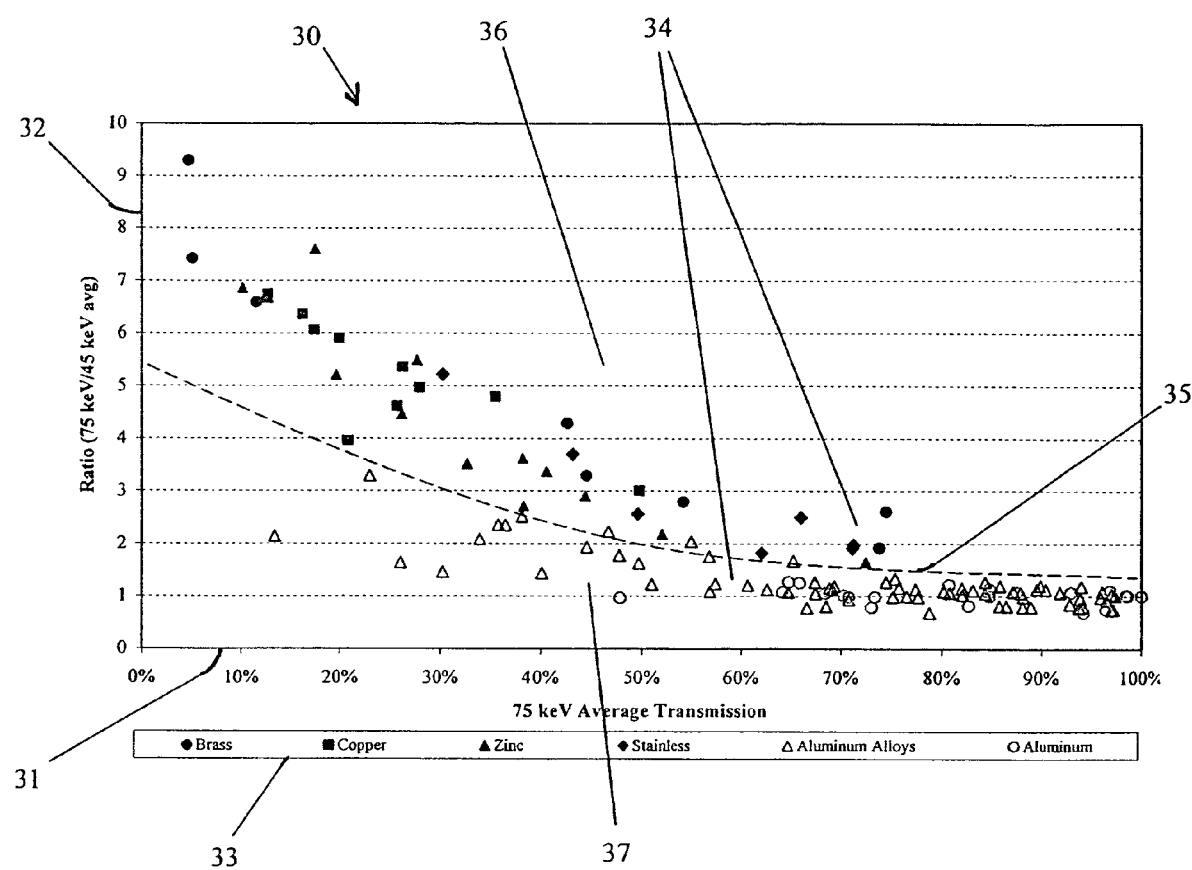
FIG. 4 shows an example graph of processed x-ray transmission data measured at two different x-ray energy levels for various nonferrous metals derived from an automobile shredder.

FIG. 4 shows an example graph 30 of processed x-ray transmission data measured for two different x-ray energy levels through various pieces of nonferrous metals derived from an automobile shredder. X-axis 31 of the graph represents normalized values of percentage transmission of x-rays (ie. transmittance values) through each metal piece as measured by the high energy detectors (item 43, FIG. 5) of array 4. Y-axis 32 of the graph represents values of the ratio (item 46, FIG. 5) of normalized values of percentage transmission of x-rays through each metal piece as measured by the high energy detectors of array 4 to the percentage transmission of x-rays through a material sample 3 as measured by the low energy detectors of array 4. In graph 30 data points 34 for the various metal samples are plotted according to their X-axis and Y-axis values. Legend 33 identifies each type data point as being for a brass, copper, zinc, stainless steel, aluminum alloy, or aluminum sample. Brass, copper, zinc, and stainless steel are considered to be relatively high Z metals and are represented by shaded data points in graph 30. Aluminum and aluminum alloys are considered to be relatively low Z metals and are represented by not shaded data points in graph 30. As can be seen in graph 30 data points for relatively high Z metals generally fall into a region 36 which resides above a region 37 into which fall data points for relatively low Z metals. A discriminator curve 35 has been drawn through the graph separating high Z region 36 from low Z region 37. This curve 35 in effect represents a preset relative composition level against which values (43,46) derived for a material sample can be compared to classify the sample as being either a relatively high Z material or as being a relatively low Z material. Other treatments of the x-ray transmission data can be utilized as well, for example locating paired logarithmic transmittance data points from the detectors in a two dimensional space with the logarithm of transmittance from the low energy detector being one axis of the space and the logarithm of transmittance from the high energy detector being the other axis. In this case a discriminator curve such as curve 35 may be found which will separate the two dimensional space into relatively high Z materials and relatively low Z materials independent of thickness of the materials. Those skilled in the art will recognize that there are numerous other methods of varying complexity for correlating data from the detectors so that regions of relative composition, such as high Z regions, low Z regions, and other Z regions can be reliably distinguished.

Figure 5:
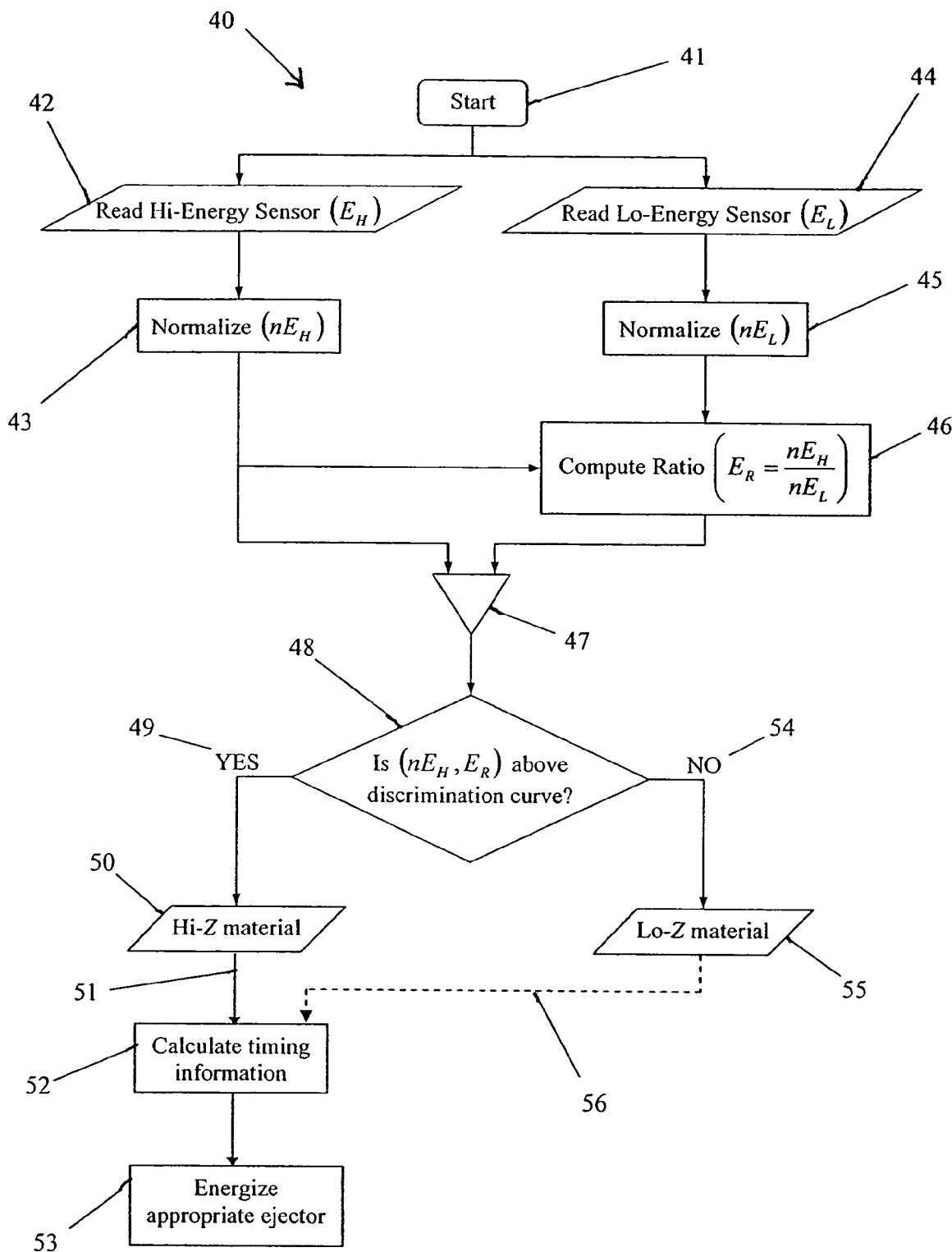
FIG. 5 shows a logic flow diagram representative of a materials identification and sorting algorithm for an embodiment of the invention.

In an embodiment of the present invention a classification and sorting algorithm 40, represented in FIG. 5, utilizes the above described type of data interpretation to classify samples as being composed of relatively high Z materials or relatively low Z materials and effects sorting of the samples accordingly. For this example a material sample 3 enters the sensing region 4s and the presence of the sample is detected by a drop in x-ray radiation received by the detectors beneath the sample at the detector array 4. This drop in radiation results in a drop in signal level from the detectors 4a. The measured drop in signal level is noted by microprocessor system 21 which is monitoring the signal levels and causes microprocessor system 21 to start 41 execution of identification and sorting algorithm 40. During execution of algorithm 40 the value $E_H$ of a high energy sensor is read 42 and the value $E_L$ of a corresponding low energy sensor is read 44. The values are normalized 43 and 45, for instance by subtracting out pre-measured detector noise and then scaling the readings to the detector readings when no materials are in region 4s over the detectors. These subtracting and scaling operations convert the sensor readings to transmittance values. Normalized value 43, (transmittance of the high energy region photons) is then divided by normalized value 45 (transmittance of low energy region photons) to compute a ratio $E_R$ 46 of high energy transmittance to low energy transmittance. Ratio 46 is then correlated with normalized high energy transmittance 43 using a correlation function 47 which is electronically equivalent to plotting a data point (43,46) onto a graph such as that of FIG. 4. Step 48 in the algorithm then computes whether correlated data (43,46) electronically lies within a relatively high Z region 36 or a relatively low Z region 37. In the example shown, if the correlated data (43,46) electronically is in a high Z region 36 algorithm 40 returns YES determination 49 and the material is categorized as a high Z material 50. In the example shown the algorithm continues along path 51, calculates 52 position and timing information for arrival of sample 3 at the ejection array 5 needed to accurately energize downstream ejector mechanisms in array 5 and issues the necessary commands 53 at the right time to energize the appropriate ejectors to eject high Z material 50 from the flow 2 of materials 3. In this case materials determined to be low Z materials 55 by algorithm 40 returning a NO determination 54 will not be ejected by ejection array 5. Alternatively, the algorithm can be configured by the user through a standard user interface to the computer system 12 to not follow path 51 and to instead follow alternate path 56 so that materials that are determined to be low Z materials 55 are ejected by ejection array 5 and materials determined to be high Z materials 50 are not ejected by ejection array 5. Those skilled in the art will recognize that other similar algorithms can be applied according to the method selected for treatment of the detector data.

All references, publications, and patents disclosed herein are expressly incorporated by reference.

For the convenience of the reader, the following is a listing of the reference numbers used in the figures:

1. Conveyor belt
2. Arrow showing flow of materials on conveyor belt
3. Materials samples
4. X-ray detector array
4*a*. Dual x-ray detector
4*b*. Data acquisition with A/D
4*c*. Electrical connection
4*s*. Sensing region on conveyor belt 1
5. Air ejectors array
5*a*. Air blast
6. Trajectory corresponding to unejected sample
7. Trajectory corresponding to ejected sample
8. Group 2 bin (for unejected samples)
9. Unejected metal sample
10. Group 1 bin (for ejected samples)
11. Selected materials for ejection by air ejectors
12. Computer system
13. Electrical connection
13*a*. Electrical connection
13*b*. Electrical connection
14. Electrical connection
15. X-ray tube
16. Sheet of collimated x-rays
17. Air ejectors controller
18. Electrical connection
20. Digital input/output (DIO) module
21. Microprocessor system
22. Computer memory 23. Serial controller
24. Digital input/output (DIO) module
30. Graph
31. X-axis of graph
32. Y-axis of graph
33. Legend to graph
34. Data points for various metal samples
35. Discriminator curve
36. High Z region of graph
37. Low Z region of graph
40. Identification and sorting algorithm
41. Start of execution of algorithm
42. High energy sensor is read
43. Normalizing value of 42
44. Low energy sensor is read
45. Normalizing value of 44
46. Computing ratio of normalized value 43 to normalized value 45
47. Correlation function
48. Determining step in algorithm 40
49. YES determination in algorithm 40
50. High Z material
51. Path in algorithm 40
52. Calculation step in algorithm 40
53. Command step in algorithm 40
54. NO determination in algorithm 40
55. Low Z material
56. Alternate path in algorithm 40

Thus, it is seen that the system and method of the present invention readily achieves the ends and advantages mentioned as well as those inherent therein. While certain preferred embodiments of the invention have been illustrated and described for purposes of the present disclosure, numerous changes in the arrangement and construction of parts may be made by those skilled in the art, which changes are encompassed within the scope and spirit of the present invention as defined by the following claims.

What is claimed is:

1. A sorting device to distinguish materials of differing relative average atomic numbers, comprising:
    an X-ray tube, wherein the X-ray tube is in a fixed position;
    a first multi-energy detector having a photon counting rate in the range of from about 1 million counts per second to about 10 million counts per second, positioned in a fixed position to receive x-rays from the X-ray tube;
    a microprocessor operationally connected to the first multi-energy detector;
    an ejector controller operationally connected to the microprocessor; and
    at least one ejector attached to the ejector controller.

2. The device of claim 1, further comprising a conveyor belt disposed between the X-ray tube and the first multi-energy detector.

3. The device of claim 1, wherein the ejector is an array of at least two ejectors.

4. The device of claim 1, further comprising at least one collection bin.

5. The device of claim 1, wherein the first multi-energy detector is a multi-energy cadmium zinc telluride pixel detection system.

6. The device of claim 5, wherein the first multi-energy detector is a multi-energy detector array for detecting more than two energy levels simultaneously, wherein the energy levels range from about 1 KeV to about 160 KeV.

7. The device of claim 6, wherein the multi-energy detector array further comprises dual energy x-ray detectors and a data acquisition system.

8. The device of claim 6, further comprising a serial controller attached to the microprocessor and attached to the multi-energy detector array.

9. The device of claim 1, wherein the microprocessor performs an identification algorithm.

10. The device of claim 1, further comprising a second multi-energy detector, wherein the second multi-energy detector is positioned in a fixed position so that it is not in the primary path of x-ray transmission.

11. A sorting device to distinguish materials of differing relative average atomic numbers, comprising:
    an X-ray tube, wherein the X-ray tube is in a fixed position;
    a first multi- energy detector having a photon counting rate of about 1 million counts per second, positioned in a fixed position to receive x-rays from the X-ray tube;
    a microprocessor operationally connected to the first multi-energy detector;
    an ejector controller operationally connected to the microprocessor; and
    at least one ejector attached to the ejector controller.

* * * * *